US009241773B2

(12) United States Patent
Bolan et al.

(10) Patent No.: US 9,241,773 B2
(45) Date of Patent: *Jan. 26, 2016

(54) IMAGING FIDUCIAL MARKERS AND METHODS

(71) Applicant: Breast-Med, Inc., Golden Valley, MN (US)

(72) Inventors: Patrick Bolan, Minneapolis, MN (US); Michael G. Garwood, Medina, MN (US); Michael T. Nelson, Golden Valley, MN (US); Daniel A. Halpern, St. Louis Park, MN (US)

(73) Assignee: Breast-Med, Inc., Golden Valley, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/634,965

(22) Filed: Mar. 2, 2015

(65) Prior Publication Data

US 2015/0173848 A1 Jun. 25, 2015

Related U.S. Application Data

(63) Continuation of application No. 14/022,539, filed on Sep. 10, 2013, now Pat. No. 8,966,735, which is a continuation of application No. 12/762,837, filed on Apr. 19, 2010, now Pat. No. 8,544,162, which is a continuation-in-part of application No. 11/281,801, filed on Nov. 17, 2005, now Pat. No. 7,702,378.

(51) Int. Cl.
*A61B 19/00* (2006.01)
*A61K 49/00* (2006.01)
(Continued)

(52) U.S. Cl.
CPC .................. *A61B 19/54* (2013.01); *A61B 8/481* (2013.01); *A61B 17/3468* (2013.01);
(Continued)

(58) Field of Classification Search
CPC .... A61B 8/481; A61B 17/3468; A61B 19/54;
A61B 2019/547; A61B 2019/5408; A61B
2019/5425; A61B 2019/5454; A61B
2019/5495; A61B 2019/5458; A61B
2019/5466; G01R 33/4814; G01R 33/5601;
A61M 31/005; A61K 49/0002; A61K
49/0447; A61K 49/18; A61K 49/226; Y10T
29/4998; Y10T 29/49982; Y10T 29/49888
See application file for complete search history.

(56) References Cited

U.S. PATENT DOCUMENTS 2,678,195 A * 5/1954 Hunter et al. ............. 74/87
5,016,639 A   5/1991 Allen
(Continued)

FOREIGN PATENT DOCUMENTS

CA   2579914 A1   11/2006
EP   1491147 A1   12/2004
(Continued)

OTHER PUBLICATIONS

"U.S. Appl. No. 11/281,801, Examiner Interview Summary mailed Sep. 2, 2009", 4 pgs.
(Continued)

*Primary Examiner* — Christopher M Koehler
(74) *Attorney, Agent, or Firm* — Schwegman Lundberg & Woessner, P.A.

(57) ABSTRACT

An implantable tissue marker incorporates a contrast agent sealed within a chamber in a container formed from a solid material. The contrast agent is selected to produce a change, such as an increase, in signal intensity under magnetic resonance imaging (MRI). An additional contrast agent may also be sealed within the chamber to provide visibility under another imaging modality, such as computed tomographic (CT) imaging or ultrasound imaging.

37 Claims, 6 Drawing Sheets

(51) Int. Cl.

| | | |
|---|---|---|
| A61K 49/04 | (2006.01) | |
| A61K 49/18 | (2006.01) | |
| A61B 8/08 | (2006.01) | |
| A61B 17/34 | (2006.01) | |
| A61K 49/22 | (2006.01) | |
| A61M 31/00 | (2006.01) | |
| G01R 33/48 | (2006.01) | |
| G01R 33/56 | (2006.01) | |
| H01F 41/02 | (2006.01) | |

(52) U.S. Cl.
CPC ........ *A61K 49/0002* (2013.01); *A61K 49/0447* (2013.01); *A61K 49/18* (2013.01); *A61K 49/223* (2013.01); *A61M 31/002* (2013.01); *A61M 31/005* (2013.01); *G01R 33/4812* (2013.01); *G01R 33/4814* (2013.01); *G01R 33/5601* (2013.01); *A61B 2019/547* (2013.01); *A61B 2019/5408* (2013.01); *A61B 2019/5425* (2013.01); *A61B 2019/5454* (2013.01); *A61B 2019/5458* (2013.01); *A61B 2019/5466* (2013.01); *A61B 2019/5495* (2013.01); *H01F 41/02* (2013.01); *H01F 41/0253* (2013.01); *Y10T 29/49075* (2015.01); *Y10T 29/4998* (2015.01); *Y10T 29/49888* (2015.01); *Y10T 29/49982* (2015.01)

(56) References Cited

U.S. PATENT DOCUMENTS

| | | | |
|---|---|---|---|
| 5,097,839 | A | 3/1992 | Allen |
| 5,119,817 | A | 6/1992 | Allen |
| 5,179,955 | A | 1/1993 | Leveen et al. |
| 5,211,164 | A | 5/1993 | Allen |
| 5,394,457 | A * | 2/1995 | Leibinger et al. ............ 378/162 |
| 5,397,329 | A * | 3/1995 | Allen ........................... 378/205 |
| 5,405,402 | A | 4/1995 | Dye et al. |
| 5,469,847 | A | 11/1995 | Zinreich et al. |
| 5,609,850 | A | 3/1997 | Deutsch et al. |
| 5,702,128 | A | 12/1997 | Maxim et al. |
| 5,769,861 | A | 6/1998 | Vilsmeier |
| 5,782,764 | A | 7/1998 | Werne |
| 6,128,522 | A | 10/2000 | Acker et al. |
| 6,161,034 | A | 12/2000 | Burbank et al. |
| 6,181,960 | B1 | 1/2001 | Jensen et al. |
| 6,269,148 | B1 | 7/2001 | Jessop et al. |
| 6,270,464 | B1 | 8/2001 | Fulton, III et al. |
| 6,333,971 | B2 | 12/2001 | McCrory et al. |
| 6,347,241 | B2 | 2/2002 | Burbank et al. |
| 6,350,244 | B1 | 2/2002 | Fisher |
| 6,356,782 | B1 | 3/2002 | Sirimanne et al. |
| 6,371,904 | B1 | 4/2002 | Sirimanne et al. |
| 6,374,132 | B1 | 4/2002 | Acker et al. |
| 6,394,965 | B1 | 5/2002 | Klein |
| 6,405,072 | B1 | 6/2002 | Cosman |
| 6,419,680 | B1 | 7/2002 | Cosman et al. |
| 6,427,081 | B1 | 7/2002 | Burbank et al. |
| 6,487,438 | B1 | 11/2002 | Widmark et al. |
| 6,516,211 | B1 | 2/2003 | Acker et al. |
| 6,544,185 | B2 | 4/2003 | Montegrande |
| 6,546,279 | B1 | 4/2003 | Bova et al. |
| 6,549,802 | B2 | 4/2003 | Thornton |
| 6,567,689 | B2 | 5/2003 | Burbank et al. |
| 6,575,991 | B1 | 6/2003 | Chesbrough et al. |
| 6,605,047 | B2 | 8/2003 | Zarins et al. |
| 6,632,176 | B2 | 10/2003 | McIntire et al. |
| 6,635,064 | B2 | 10/2003 | U et al. |
| 6,656,192 | B2 | 12/2003 | Espositio et al. |
| 6,662,041 | B2 | 12/2003 | Burbank et al. |
| 6,699,205 | B2 | 3/2004 | Fulton, III et al. |
| 6,725,083 | B1 | 4/2004 | Burbank et al. |
| 6,730,042 | B2 | 5/2004 | Fulton et al. |
| 6,746,661 | B2 | 6/2004 | Kaplan |
| 6,761,679 | B2 | 7/2004 | Sajo et al. |
| 6,773,408 | B1 | 8/2004 | Acker et al. |
| 6,778,850 | B1 | 8/2004 | Adler et al. |
| 6,862,470 | B2 | 3/2005 | Burbank et al. |
| 6,927,406 | B2 | 8/2005 | Zyromski |
| 6,993,375 | B2 | 1/2006 | Burbank et al. |
| 6,996,433 | B2 | 2/2006 | Burbank et al. |
| 7,010,340 | B2 | 3/2006 | Scarantino et al. |
| 7,044,957 | B2 | 5/2006 | Foerster et al. |
| 7,047,063 | B2 | 5/2006 | Burbank et al. |
| 7,226,442 | B2 | 6/2007 | Sheppard, Jr. et al. |
| 7,668,582 | B2 * | 2/2010 | Sirimanne et al. ............ 600/414 |
| 7,702,378 | B2 * | 4/2010 | Bolan et al. .................. 600/414 |
| 7,792,568 | B2 * | 9/2010 | Zhong et al. ................. 600/431 |
| 8,280,486 | B2 * | 10/2012 | Miller et al. ................. 600/414 |
| 8,544,162 | B2 * | 10/2013 | Bolan et al. ..................... 29/460 |
| 8,966,735 | B2 * | 3/2015 | Bolan et al. ..................... 29/460 |
| 2002/0035324 | A1 * | 3/2002 | Sirimanne et al. ............ 600/431 |
| 2002/0083591 | A1 | 7/2002 | Geertsma et al. |
| 2002/0083951 | A1 * | 7/2002 | Stegmaier et al. ............ 128/899 |
| 2002/0107437 | A1 * | 8/2002 | Sirimanne et al. ............ 600/407 |
| 2002/0161298 | A1 | 10/2002 | Burbank et al. |
| 2002/0188196 | A1 | 12/2002 | Burbank et al. |
| 2004/0030262 | A1 * | 2/2004 | Fisher et al. .................. 600/564 |
| 2004/0176684 | A1 * | 9/2004 | Tabuchi et al. ............... 600/424 |
| 2004/0186377 | A1 * | 9/2004 | Zhong et al. ................. 600/431 |
| 2004/0193044 | A1 | 9/2004 | Burbank et al. |
| 2004/0236211 | A1 | 11/2004 | Burbank et al. |
| 2004/0236212 | A1 | 11/2004 | Jones et al. |
| 2004/0236213 | A1 | 11/2004 | Jones et al. |
| 2005/0004456 | A1 | 1/2005 | Thomas et al. |
| 2005/0020916 | A1 | 1/2005 | MacFarlane et al. |
| 2005/0033157 | A1 | 2/2005 | Klein et al. |
| 2005/0059884 | A1 | 3/2005 | Kragg |
| 2005/0059888 | A1 * | 3/2005 | Sirimanne et al. ............ 600/431 |
| 2005/0065393 | A1 | 3/2005 | Miller |
| 2005/0080337 | A1 * | 4/2005 | Sirimanne et al. ............ 600/431 |
| 2005/0080338 | A1 * | 4/2005 | Sirimanne et al. ............ 600/431 |
| 2005/0080339 | A1 * | 4/2005 | Sirimanne et al. ............ 600/431 |
| 2005/0085724 | A1 * | 4/2005 | Sirimanne et al. ............ 600/431 |
| 2005/0143656 | A1 | 6/2005 | Burbank et al. |
| 2005/0154293 | A1 * | 7/2005 | Gisselberg et al. ........... 600/420 |
| 2005/0205445 | A1 | 9/2005 | Seiler et al. |
| 2005/0234336 | A1 | 10/2005 | Beckman et al. |
| 2005/0255045 | A1 | 11/2005 | Woltering |
| 2006/0036165 | A1 | 2/2006 | Burbank et al. |
| 2006/0058645 | A1 | 3/2006 | Komistek et al. |
| 2006/0058648 | A1 | 3/2006 | Meier et al. |
| 2006/0079805 | A1 | 4/2006 | Miller et al. |
| 2006/0084865 | A1 | 4/2006 | Burbank et al. |
| 2006/0122503 | A1 | 6/2006 | Burbank et al. |
| 2006/0155190 | A1 | 7/2006 | Burbank et al. |
| 2006/0173296 | A1 | 8/2006 | Miller et al. |
| 2006/0293581 | A1 | 12/2006 | Plewes et al. |
| 2007/0087026 | A1 | 4/2007 | Field |
| 2007/0093726 | A1 | 4/2007 | Leopold et al. |
| 2007/0110665 | A1 | 5/2007 | Bolan et al. |
| 2007/0118034 | A1 | 5/2007 | Mark |
| 2007/0142725 | A1 | 6/2007 | Hardin et al. |
| 2008/0033286 | A1 | 2/2008 | Whitmore et al. |
| 2008/0234572 | A1 | 9/2008 | Jones |
| 2008/0269603 | A1 | 10/2008 | Nicoson et al. |
| 2009/0069670 | A1 | 3/2009 | Mark |
| 2009/0105584 | A1 | 4/2009 | Jones |
| 2010/0030072 | A1 * | 2/2010 | Casanova et al. ............ 600/431 |
| 2010/0287887 | A1 | 11/2010 | Bolan et al. |
| 2013/0046164 | A1 | 2/2013 | Liu et al. |
| 2013/0150707 | A1 | 6/2013 | Cima et al. |
| 2013/0324946 | A1 | 12/2013 | Tobias et al. |
| 2014/0187911 | A1 | 7/2014 | Bolan et al. |

FOREIGN PATENT DOCUMENTS

| | | |
|---|---|---|
| EP | 1579878 A1 | 9/2005 |
| EP | 1847845 A1 | 10/2007 |
| WO | WO-9717103 A1 | 5/1997 |
| WO | WO-0024332 A1 | 5/2000 |
| WO | WO-0038579 A2 | 7/2000 |
| WO | WO-0230482 A1 | 4/2002 |

(56) References Cited

FOREIGN PATENT DOCUMENTS

| WO | WO-03022133 A2 | 3/2003 |
|---|---|---|
| WO | WO-03051452 A1 | 6/2003 |
| WO | WO-2004084738 A1 | 10/2004 |
| WO | WO-2005046733 A1 | 5/2005 |
| WO | WO-2005063126 A2 | 7/2005 |
| WO | WO-2006044132 A1 | 4/2006 |
| WO | WO-2006119645 A1 | 11/2006 |
| WO | WO-2007060576 A2 | 5/2007 |

OTHER PUBLICATIONS

"U.S. Appl. No. 11/281,801, Final Office Action mailed Mar. 13, 2009", 18 pgs.
"U.S. Appl. No. 11/281,801, Non-Final Office Action mailed Sep. 22, 2008", 12 pgs.
"U.S. Appl. No. 11/281,801, Notice of Allowance mailed Dec. 2, 2009", 10 pgs.
"U.S. Appl. No. 11/281,801, Response filed Dec. 18, 2008 to Non-Final Office Action mailed Sep. 22, 2008", 25 pgs.
"U.S. Appl. No. 11/281,801, Response filed Jun. 12, 2009 to Final Office Action mailed Mar. 13, 2009", 27 pgs.
"U.S. Appl. No. 11/281,801, Response filed Jul. 17, 2008 to Restriction Requirement mailed Apr. 17, 2008", 13 pgs.
"U.S. Appl. No. 11/281,801, Restriction Requirement mailed Apr. 17, 2008", 5 pgs.
"U.S. Appl. No. 11/281,801, Supplemental Response filed Aug. 24, 2009 to Final Office Action mailed Mar. 13, 2009", 29 pgs.
"U.S. Appl. No. 11/281,801, Supplemental Response filed Aug. 25, 2009 to Final Office Action mailed Mar. 13, 2009", 2 pgs.
"U.S. Appl. No. 11/281,801, Supplemental Response filed Aug. 28, 2009 to Final Office Action mailed Mar. 13, 2009", 16 pgs.
"U.S. Appl. No. 12/762,837, Non Final Office Action mailed Nov. 2, 2012", 15 pgs.
"U.S. Appl. No. 12/762,837, Notice of Allowance mailed May 30, 2013", 6 pgs.
"U.S. Appl. No. 12/762,837, Response filed Jan. 18, 2013 to Non Final Office Action mailed Nov. 2, 2012", 14 pgs.
"U.S. Appl. No. 14/022,539, Final Office Action mailed Jul. 24, 2014", 7 pgs.
"U.S. Appl. No. 14/022,539, Non Final Office Action mailed Apr. 11, 2014", 8 pgs.
"U.S. Appl. No. 14/022,539, Notice of Allowance mailed Oct. 24, 2014", 10 pgs.
"U.S. Appl. No. 14/022,539, Preliminary Amendment filed Mar. 10, 2014", 8 pgs.
"U.S. Appl. No. 14/022,539, Response filed Jul. 11, 2014 to Non Final Office Action mailed Apr. 11, 2014", 10 pgs.
Bolan, P. J., et al., "A Novel Soft Tissue Marker for Multimodal Breast Imagine with Positive MRI Contrast", Joint Annual Meeting ISMRM-ESMRMB, (May 2007), 1 pg.
Bolan, Patrick, "A Novel Tissue Marker for Multimodal Breast Imaging (Abstract)", Abstract submitted Apr. 2005, published Radiological Society of North America (RSNA), Nov. 2005., [Online]. Retrieved from the Internet: <URL: http://abstract.rsna.org/index.cfm?fuseaction=submission.popupPrevie . . . >, (Nov. 2005), 2 pgs.
Bolan, Patrick, "Soft Tissue Markers or Clips (Presentation)", This work was supported under NIH grants, the MIND institute, and the Keck Foundation., (Nov. 16, 2005), 16 pgs.
Ellis, R. E., et al., "Use of Biocompatible Fiducial Marker in Evaluating the Accuracy of CT Image Registration", Investigative Radiology, (1996), 1-9.
Frank, Steven J., et al., "A Novel MRI Marker for Prostate Brachytherapy", Int. J. Radiation Oncology Biol. Phys., vol. 70, No. 1, (2008), 5-8.
Gierga, D. P., et al., "The Correlation between Internal and External Markers for Abdominal Tumors: Implications for Respiratory Gating", Int J Radiat Oncol Biol Phys.; 61 (f); 1551-8, (Apr. 1, 2005), 1 pg.
Igdem, S., et al., "Implantation of Fiducial Markers for Image Guidance in Prostate Radiotherapy: Patient-reported toxicity", The British Journal of Radiology, (2009), 1-5.
Maier-Hein, L, et al., "On Combining Internal and External Fiducials for Liver Motion Compensation", Comput Aided Surg.; 13(6): 369-76, (Nov. 2008), 1 pg.

\* cited by examiner

IMAGING FIDUCIAL MARKERS AND METHODS

RELATED APPLICATIONS

This application is a continuation of U.S. patent application Ser. No. 14/022,539, filed on Sep. 10, 2013, which is a continuation of U.S. Ser. No. 12/762,837, filed on Apr. 19, 2010, which is a Continuation-in-Part of U.S. application Ser. No. 11/281,801, filed Nov. 17, 2005, and issued as U.S. Pat. No. 7,702,378 on Apr. 20, 2010, all of which are incorporated herein by reference in their entireties and the benefit of priority of each of which is claimed herein.

TECHNICAL BACKGROUND

The disclosure relates generally to tissue markers. More particularly, the disclosure relates to implantable tissue markers for use in magnetic resonance imaging.

BACKGROUND

Certain medical conditions, including breast cancer, are increasingly being diagnosed and treated using minimally invasive medical techniques. Such techniques typically involve the use of clinical imaging methods that allow the physician to visualize interior portions of a patient's body without the need to make excessive incisions or cause avoidable collateral damage to healthy adjacent tissue. Imaging can be performed using any of variety of modalities, including, for example, X-rays, computed tomographic (CT) X-ray imaging, fluoroscopy, portal film imaging devices, electronic portal imaging devices, ultrasound, electrical impedance tomography (EIT), magnetic resonance (MR) imaging, or MRI, magnetic source imaging (MSI), magnetic resonance spectroscopy (MRS), magnetic resonance mammography (MRM), magnetic resonance angiography (MRA), magneto-electro-encephalography (MEG), laser optical imaging, electric potential tomography (EPT), brain electrical activity mapping (BEAM), arterial contrast injection angiography, and digital subtraction angiography. Nuclear medicine modalities include positron emission tomography (PET) and single photon emission computed tomography (SPECT).

Some of these imaging procedures involve the use of radiographic markers. Radiographic markers are small devices that are implanted in a patient during surgical procedures, such as biopsies. Conventional markers typically consist of one or more solid objects, such as a piece of metallic wire, ceramic beads, etc., which are implanted either by themselves or within a gelatinous matrix, collagen, or polylactic acid, to temporarily increase visibility, for example, to ultrasound imaging. They are designed to be visible to one of the imaging modalities listed above and typically have a shape that is readily identifiable as an artificial structure, as contrasted from naturally occurring anatomical structures in the patient's body. For example, markers can be shaped as coils, stars, rectangles, spheres, or other shapes that do not occur in anatomical structures. Such markers enable radiologists to localize the site of surgery in subsequent imaging studies or to facilitate image registration during image-guided therapeutic procedures. In this way, markers can serve as landmarks that provide a frame of reference for the radiologist.

Most conventional markers appear as a signal void, i.e., a dark artifact, in magnetic resonance imaging. This manifestation can be particularly problematic in some contexts. For example, heterogeneous breast tissue produces many dark artifacts under MR imaging, thereby rendering small signal voids produced by some conventional markers difficult to identify and distinguish from naturally occurring dark artifacts. In addition, some markers produce large susceptibility artifacts under MR imaging, thereby distorting images in both MRI and spectroscopic modalities. Some markers incorporate an external gel that may produce a positive or bright signal, but such gels are not permanent. Some other markers contain collagen or polylactic acid, which may interfere with magnetic resonance spectroscopy. With the increasing use of MR imaging techniques in the treatment of breast cancer in clinical settings, improved MR visibility of tissue markers is particularly desirable.

SUMMARY OF THE DISCLOSURE

According to various example embodiments, an implantable tissue marker incorporates a contrast agent sealed within a chamber in a container formed from a solid material. The contrast agent is selected to produce a change in signal intensity under magnetic resonance imaging (MRI). An additional contrast agent may also be sealed within the chamber to provide visibility under another imaging modality, such as computed tomographic (CT) imaging or ultrasound imaging.

One embodiment is directed to a permanently implantable radiographic marker. A container formed from a solid material defines an internal chamber, in which a contrast agent is sealed. The contrast agent is selected to produce an increase in signal intensity in a magnetic resonance (MR) imaging modality. Another embodiment is directed to a method of manufacturing such a marker.

In another embodiment, a permanently implantable fiducial marker includes a container formed from a nonbiodegradable solid material. The container defines an internal chamber. A first contrast agent is sealed within the internal chamber and is selected to produce an increase in signal intensity in a magnetic resonance (MR) imaging modality. A second contrast agent sealed within the internal chamber. The second contrast agent is selected to produce a signal in another imaging modality.

Another embodiment is directed to a method of identifying a location within a body of a patient. A marker is implanted proximate the location. The marker comprises a container formed from a solid material and defining an internal chamber, and a contrast agent sealed within the internal chamber. The contrast agent is selected to produce an increase in signal intensity in a magnetic resonance (MR) imaging modality. A first image of the location is generated in the magnetic resonance (MR) imaging modality.

Various embodiments may provide certain advantages. For instance, a contrast agent selected to produce an increase in signal intensity in an MR imaging modality may produce good visualization characteristics without also producing an excessive artifact and without interfering with MR spectroscopy or diffusion imaging. Production of an increase in signal intensity in an MR imaging modality may be particularly beneficial in certain contexts, such as, for example, imaging of breast tissue, which is heterogeneous.

Additional objects, advantages, and features will become apparent from the following description and the claims that follow, considered in conjunction with the accompanying drawings.

DESCRIPTION OF VARIOUS EMBODIMENTS

According to various embodiments, an implantable tissue marker incorporates a contrast agent sealed within a chamber in a container formed from a solid material. The contrast agent is selected to produce an increase in signal intensity under magnetic resonance imaging (MRI). An additional contrast agent may also be sealed within the chamber to provide visibility under another imaging modality, such as computed tomographic (CT) imaging or ultrasound imaging.

In this way, certain advantages may be realized. For instance, a contrast agent selected to produce an increase in signal intensity in an MR imaging modality may produce good visualization characteristics without also producing an excessive artifact and without interfering with MR spectroscopy or diffusion imaging. Producing an increase in signal intensity in an MR imaging modality may be particularly beneficial in certain contexts, such as, for example, imaging of breast tissue. Most conventional markers appear as a signal void in MR imaging. The heterogeneous nature of breast tissue makes small signal voids difficult to identify. By producing an increase in signal intensity, i.e., a bright area, in MR imaging, the implantable tissue markers disclosed herein may be easier to see than conventional markers.

The following description of various embodiments implemented in the context of imaging certain types of tissue is to be construed by way of illustration rather than limitation. This description is not intended to limit the invention or its applications or uses. For example, while various embodiments are described as being implemented in the context of imaging breast tissue, it will be appreciated that the principles of the disclosure are applicable to other contexts, such as image registration during image guided therapeutic procedures. In further examples, while various embodiments are described as being implemented in the context of imaging breast tissue, it will be appreciated that the principles of the disclosure are applicable to other anatomical sites, such as prostate, brain, spinal, and other anatomical sites.

In the following description, numerous specific details are set forth in order to provide a thorough understanding of various embodiments. It will be apparent to one skilled in the art that some embodiments may be practiced without some or all of these specific details. In other instances, well known components and process steps have not been described in detail.

Figure 1:
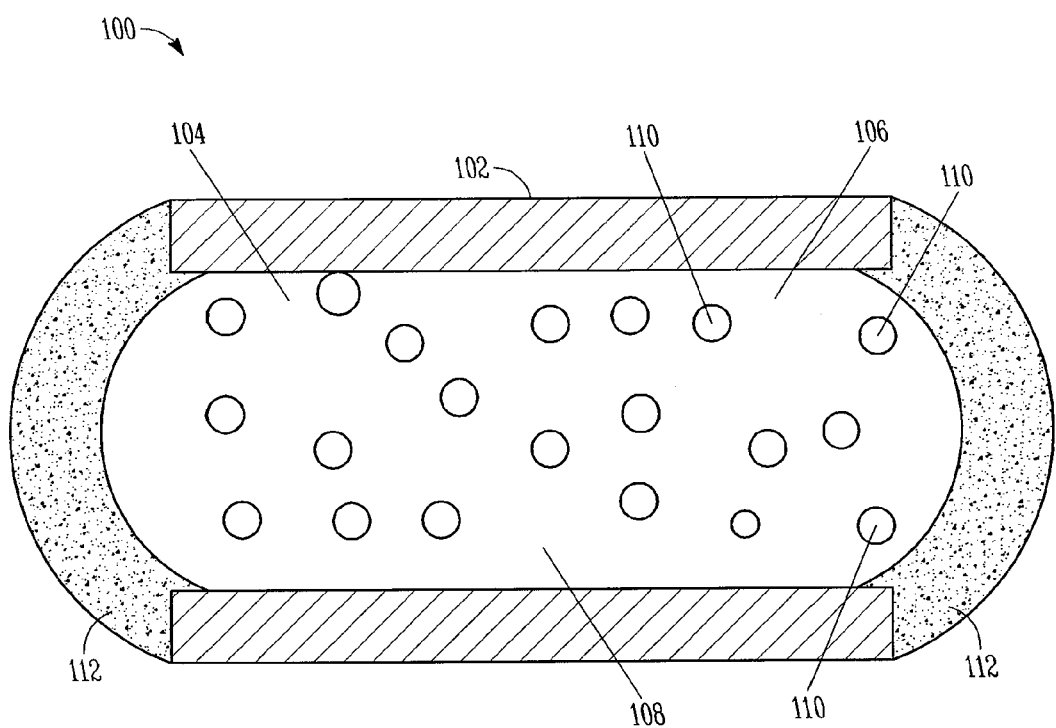
FIG. 1 is a sectional view of a tissue marker according to one embodiment.

Referring now to the drawings, FIG. 1 is a sectional view illustrating an example implantable radiographic marker 100 according to one embodiment. A tube 102 is formed from a nonbiodegradable radiopaque solid material, such as glass, plastic, carbon fiber, or silicone. For example, the tube 102 may be formed from LEXAN® polycarbonate resin, commercially available from General Electric Company, headquartered in Pittsfield, Mass. The tube 102 is preferably sized for insertion via a biopsy cannula. For example, in one particular implementation, the tube 102 has a major dimension of approximately 3-4 mm and a minor dimension of approximately 1-2 mm.

The tube 102 defines two end portions 104 and 106, at least one of which is initially open. A chamber 108 is defined within the tube 102 between the two end portions 104 and 106. One or more contrast agents 110 are introduced into the chamber 108. The end portions 104 and 106 are then sealed, for example, using a sealant 112 such as epoxy. In some embodiments, a permanent biocompatible adhesive such as cyanoacrylate serves as the sealant 112.

The visual representation of the contrast agents 110 in FIG. 1 is intended only to distinguish the contrast agents 110 from the chamber 108 in which they are disposed. According to various embodiments, the contrast agents 110 can be implemented as a gas, gel, or liquid, or as a combination of gases, gels, and/or liquids. Each of these materials can be selected independently to customize the appearance of the marker 100 in different imaging modalities and under different conditions, e.g., with or without contrast, and in various tissue types.

For instance, if the marker 100 is to be visible in magnetic resonance (MR) and computed tomographic (CT) imaging modalities, the chamber 108 may contain a mixture of a gadolinium-DTPA MR contrast agent and an iodinated CT contrast agent. The volume of contrast agent 110 in the chamber 108 may be maximized to promote visibility. Visibility is also promoted by matching the magnetic susceptibility of the contrast agent 110 and the magnetic susceptibility of the tube 102. If it is further desired that the marker 100 be visible in an ultrasound imaging modality, the chamber 108 may also contain a gas bubble.

In some embodiments, the tube 102 itself, rather than multiple contrast agents 110, may provide visibility in certain imaging modalities. For example, the tube 102 may be made of a radiopaque polymer that provides contrast in X-ray imaging modalities. As another example, a difference in acoustic impedance between the tube 102 and the material in the chamber 108 will cause the marker 100 to reflect ultrasound waves, thereby promoting visibility in an ultrasound imaging modality. Further, if the magnetic susceptibility of the tube 102 is similar to that of the material in the chamber 108 and to that of the surrounding tissue, visibility in MR imaging modalities will be improved due to improved magnetic field homogeneity and reduced $T_2^*$ artifact.

In one particular embodiment, the marker 100 is formed by cutting a glass micropipette, commercially available from Fisher Scientific, headquartered in Hampton, N.H., to the desired length, e.g., 4 mm, to form the tube 102. The micropipette has an outer diameter appropriate for insertion via a biopsy cannula, e.g., 2 mm.

Contrast agents 110 are then introduced into the chamber 108 defined by the tube 102. In one particular embodiment, for example, an MR contrast agent and a CT contrast agent are combined, and the liquid mixture resulting from this combination is injected into the micropipette via a syringe of appropriate gauge, e.g., 25 ga. The MR contrast agent may be implemented as a gadolinium-based MR contrast agent, such as MAGNEVIST® MR contrast agent, commercially available from Berlex, headquartered in Montville, N.J. Other MR contrast agents include, but are not limited to, OMNISCAN™ MR contrast agent, commercially available from GE Healthcare, headquartered in Chalfont St. Giles, United Kingdom, PROHANCE® MR contrast agent, and OPTIMARK® MR contrast agent, commercially available from Tyco Healthcare/Mallinckrodt, Inc., headquartered in St. Louis, Mo. The CT contrast agent may be implemented as an iodinated CT contrast agent, such as OMNIPAQUE™ CT contrast agent, commercially available from GE Healthcare, headquartered in Chalfont St. Giles, United Kingdom. Other CT contrast agents include, but are not limited to, HEXABRIX®, TELEBRIX®, and CONRAY® CT contrast agents, commercially available from Tyco Healthcare/Mallinckrodt, Inc., headquartered in St. Louis, Mo. After the mixture is injected in the chamber 108, the ends of the tube 102 are sealed using a quick-setting epoxy.

Markers 100 of the type illustrated in FIG. 1 and described above have been evaluated for visibility in multiple imaging modalities. Markers 100 were made according to the above-described procedure and were suspended in a gelatin phantom. Magnetic resonance imaging (MRI) was performed on the gelatin phantom using a Siemens Trio 3T (3 Tesla) human MRI scanner. The MRI process used $T_1$-weighted 3D fast low angle shot (FLASH) images, which are typical for MR examinations of breast tissue. In addition, the gelatin phantom was also imaged using a clinical breast X-ray mammography system and a breast ultrasound using standard settings.

Figure 4:
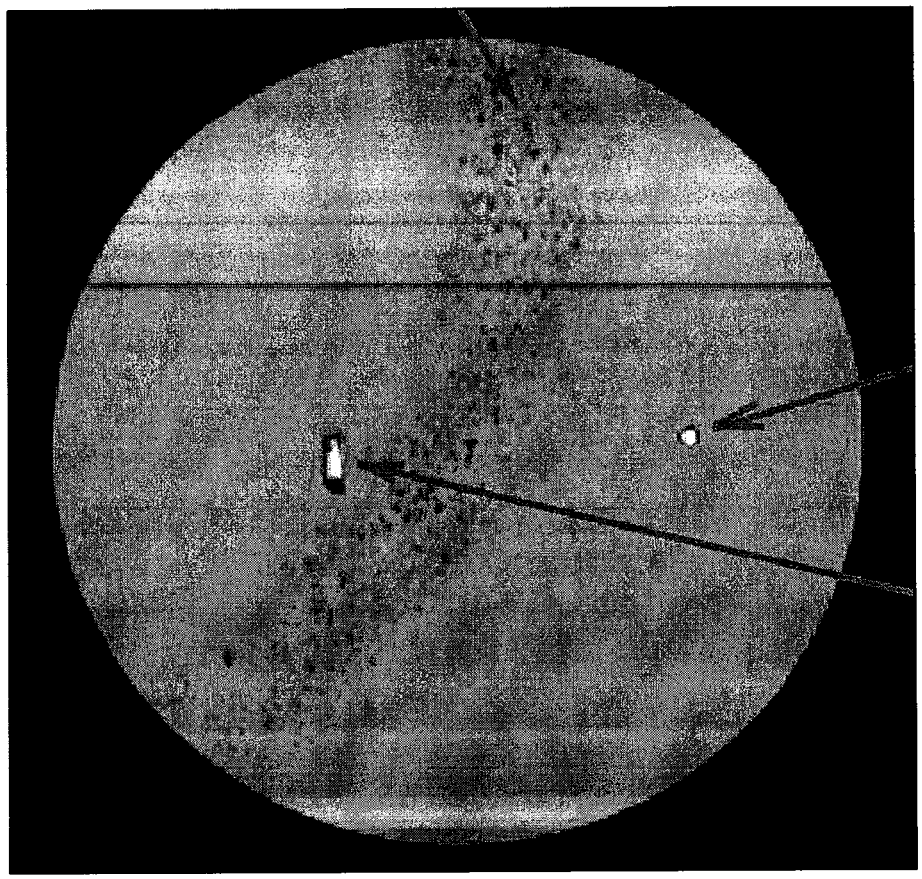
FIG. 4 is an image of the tissue marker of FIG. 1 as visible in a magnetic resonance imaging (MRI) modality.
Figure 5:
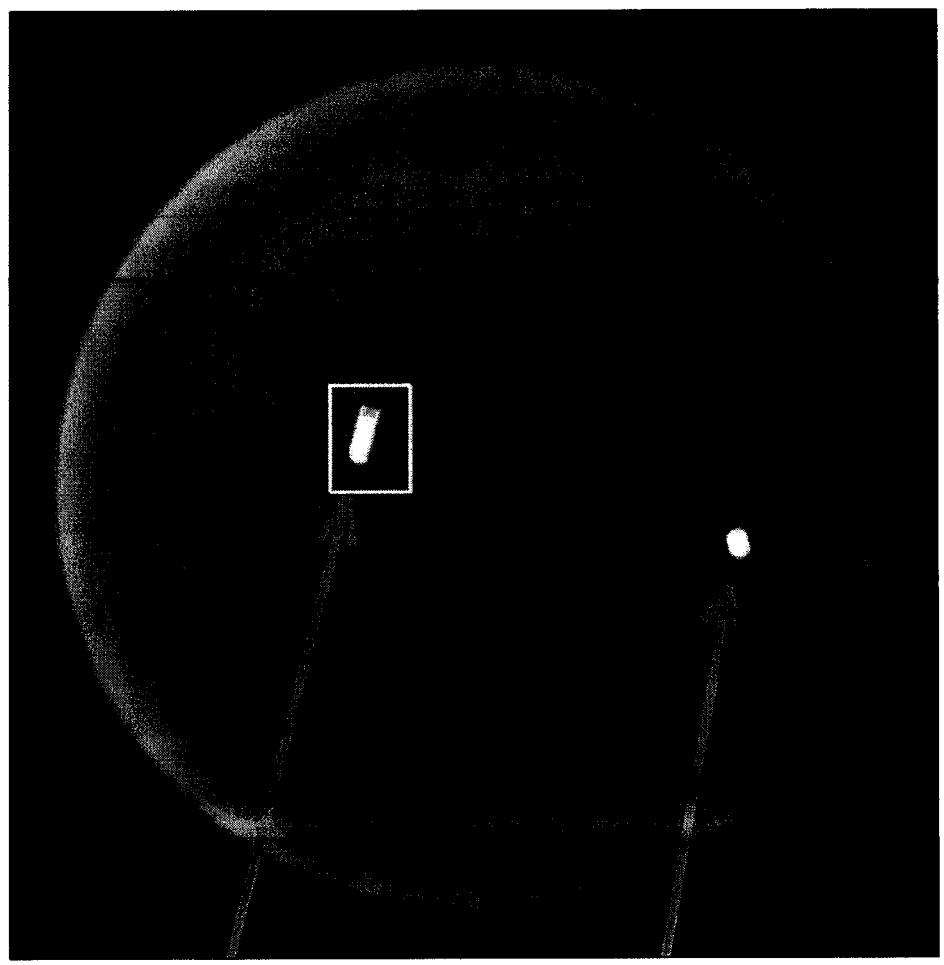
FIG. 5 is an image of the tissue marker of FIG. 1 as visible in an x-ray mammography modality.
Figure 6:
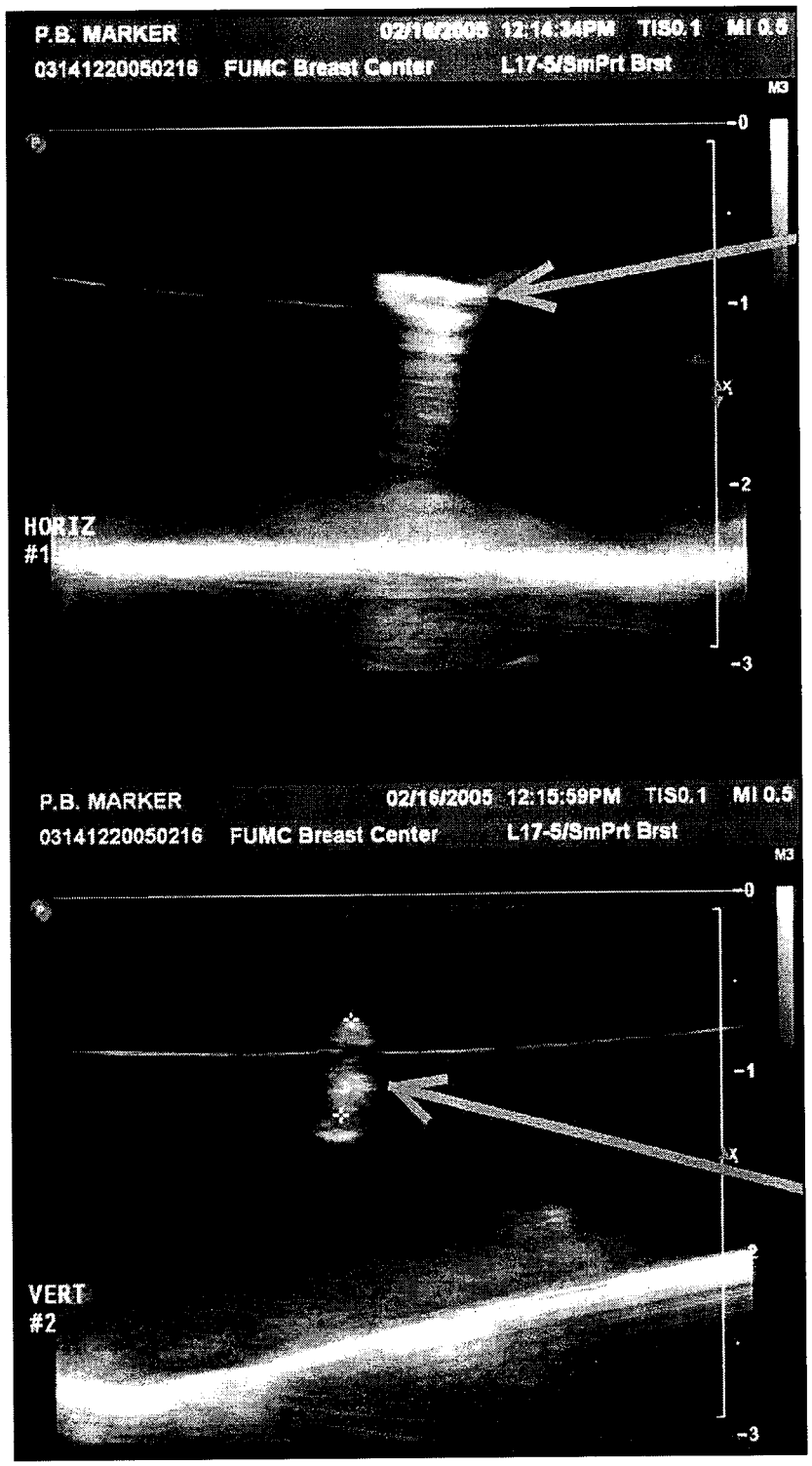
FIG. 6 is an image of the tissue marker of FIG. 1 as visible in an ultrasound imaging modality.

The evaluation of the markers 100 demonstrated that the markers 100 were clearly visible on the three modalities, namely, MRI, X-ray mammography, and ultrasound. FIGS. 4-6 are images of markers 100 obtained under the MRI, X-ray mammography, and ultrasound modalities, respectively. The markers 100 appeared as small signal voids, i.e., dark spots, under low-resolution MRI (0.8 mm in plane). However, the contrast agent 110 in the chamber 108 appeared hyperintense, that is, as bright spots, under higher MRI resolutions, e.g., 0.4 mm in plane. Accordingly, using higher MRI resolutions, the markers 100 are more clearly distinguishable from surrounding tissue than conventional markers that appear as signal voids. The bright signal seen at higher MRI resolutions may be particularly advantageous in imaging heterogeneous breast tissue, in which signal voids may be difficult to see.

In addition to the MRI modality, the markers 100 were also visible in the X-ray mammography and ultrasound imaging modalities. In the X-ray mammography modality, the radiopaque liquid occupying the chamber 108 could be seen clearly with distinct edges. In the ultrasound modality, the tube 102 appeared hyperechoic, while the contrast agents 110 occupying the chamber 108 appeared dark. In this modality, the markers 100 were most easily seen when they were oriented parallel to the transducer surface. However, the markers 100 could also be detected when they were oriented perpendicular to the transducer surface.

According to various embodiments, the contrast agents 110 that are sealed within the chamber 108 can be selected for visibility in any of a number of imaging modalities. Besides the MR, X-ray, and ultrasound imaging modalities mentioned above, contrast agents can be selected for visibility in computed tomographic (CT) X-ray imaging, fluoroscopy, portal film imaging, electronic portal imaging, electrical impedance tomography (EIT), magnetic source imaging (MSI), magnetic resonance spectroscopy (MRS), magnetic resonance mammography (MRM), magnetic resonance angiography (MRA), magnetoelectro-encephalography (MEG), laser optical imaging, electric potential tomography (EPT), brain electrical activity mapping (BEAM), arterial contrast injection angiography, and digital subtraction angiography modalities. Nuclear medicine modalities include positron emission tomography (PET) and single photon emission computed tomography (SPECT). In addition, as additional imaging modalities are developed in the future, it will be possible to seal contrast agents within the chamber 108 that are selected for visibility in such future modalities.

Figure 2:
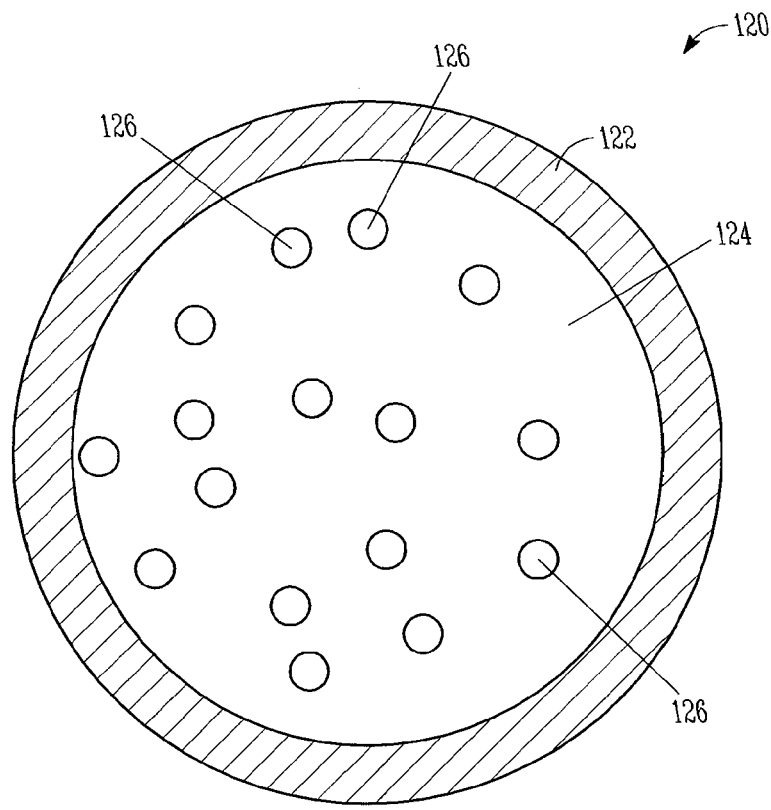
FIG. 2 is a sectional view of a tissue marker according to another embodiment.

FIG. 2 is a sectional view of another example tissue marker 120 according to another embodiment. The tissue marker 120 incorporates an outer capsule 122 formed from a nonbiodegradable radiopaque solid material, such as silicone. The capsule 122 is generally spherical in shape and is preferably sized for insertion via a biopsy cannula. The capsule 122 defines an internal chamber 124.

One or more contrast agents 126 are introduced into the chamber 124, for example, by injecting the contrast agents 126 into the chamber 124. The visual representation of the contrast agents 126 in FIG. 2 is intended only to distinguish the contrast agents 126 from the chamber 124 in which they are disposed. According to various embodiments, the contrast agents 126 can be implemented as a gas, gel, or liquid, or as a combination of gases, gels, and/or liquids. Each of these materials can be selected independently to customize the appearance of the marker 120 in different imaging modalities and under different conditions, e.g., with or without contrast, and in various tissue types. For instance, if the marker 120 is to be visible in magnetic resonance (MR) and computed tomographic (CT) imaging modalities, the chamber 124 may contain a mixture of a gadolinium-DTPA MR contrast agent, such as MAGNEVIST® MR contrast agent, and an iodinated CT contrast agent, such as OMNIPAQUE™ CT contrast agent. The volume of contrast agent 126 in the chamber 124 may be maximized to promote visibility. Visibility is also promoted by matching the magnetic susceptibility of the contrast agent 126 and the magnetic susceptibility of the capsule 122. If it is further desired that the marker 120 be visible in an ultrasound imaging modality, the chamber 124 may also contain an air bubble. After the mixture is injected in the chamber 124, the capsule 122 is sealed.

In some embodiments, the capsule 122 itself, rather than multiple contrast agents 126, may provide visibility in certain imaging modalities. For example, the capsule 122 may be made of a radiopaque polymer that provides contrast in X-ray imaging modalities. As another example, a difference in acoustic impedance between the capsule 122 and the material in the chamber 124 will cause the marker 120 to reflect ultrasound waves, thereby promoting visibility in an ultrasound imaging modality. Further, if the magnetic susceptibility of the capsule 122 is similar to that of the material in the chamber 124 and to that of the surrounding tissue, visibility in MR imaging modalities will be improved due to reduction of $T_2$ darkening.

Figure 3:
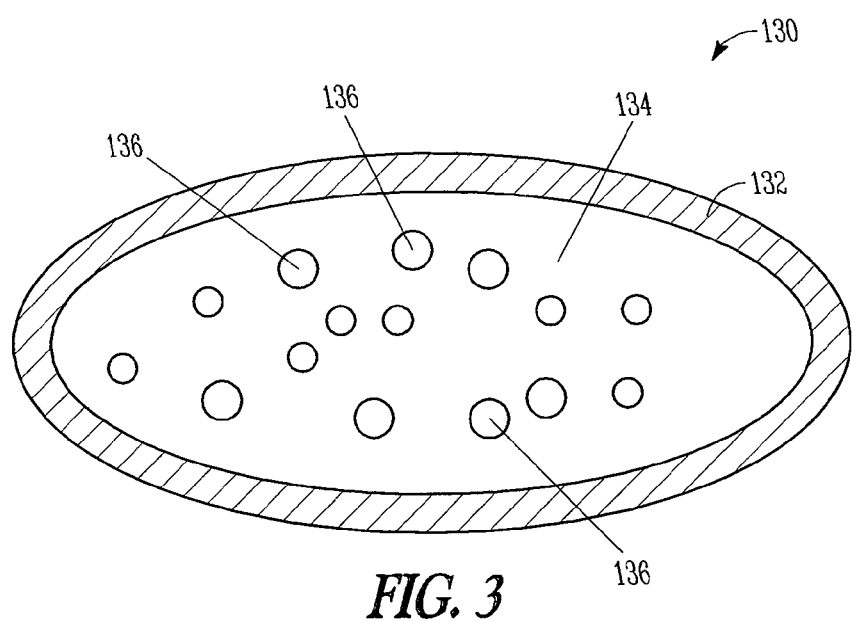
FIG. 3 is a sectional view of a tissue marker according to yet another embodiment.

FIG. 3 is a sectional view of another example tissue marker 130 according to another embodiment. The tissue marker 130 incorporates an outer capsule 132 formed from a nonbiodegradable radiopaque solid material, such as silicone. The capsule 132 is generally spheroid in shape and is preferably sized for insertion via a biopsy cannula. The capsule 132 defines an internal chamber 134.

One or more contrast agents 136 are introduced into the chamber 134, for example, by injecting the contrast agents 136 into the chamber 134. The visual representation of the contrast agents 136 in FIG. 3 is intended only to distinguish the contrast agents 136 from the chamber 134 in which they are disposed. According to various embodiments, the contrast agents 136 can be implemented as a gas, gel, or liquid, or as a combination of gases, gels, and/or liquids. Each of these materials can be selected independently to customize the appearance of the marker 130 in different imaging modalities and under different conditions, e.g., with or without contrast, and in various tissue types. For instance, if the marker 130 is to be visible in magnetic resonance (MR) and computed tomographic (CT) imaging modalities, the chamber 134 may contain a mixture of a gadolinium-DTPA MR contrast agent, such as MAGNEVIST® MR contrast agent, and an iodinated CT contrast agent, such as OMNIPAQUE™ CT contrast agent. The volume of contrast agent 136 in the chamber 134 may be maximized to promote visibility. Visibility is also promoted by matching the magnetic susceptibility of the contrast agent 136 and the magnetic susceptibility of the capsule 132. If it is further desired that the marker 130 be visible in an ultrasound imaging modality, the chamber 134 may also contain an air bubble. After the mixture is injected in the chamber 134, the capsule 132 is sealed.

In some embodiments, the capsule 132 itself, rather than multiple contrast agents 136, may provide visibility in certain imaging modalities. For example, the capsule 132 may be made of a radiopaque polymer that provides contrast in X-ray imaging modalities. As another example, a difference in acoustic impedance between the capsule 132 and the material in the chamber 134 will cause the marker 130 to reflect ultrasound waves, thereby promoting visibility in an ultrasound imaging modality. Further, if the magnetic susceptibility of the capsule 132 is similar to that of the material in the chamber 134 and to that of the surrounding tissue, visibility in MR imaging modalities will be improved due to reduction of $T_2$ darkening.

The markers 100, 120, and 130 illustrated in FIGS. 1-3 can be used for imaging a location within a patient's body. One or more markers are implanted near the location via, for example, a biopsy cannula. The markers can be implanted using any of a variety of conventional techniques, including, but not limited to, non-invasive medical procedures, biopsy procedures, injection, and conventional surgical procedures. In addition, the markers can be guided to a desired anatomical site during implantation using one or more imaging modalities in which the markers are detectable. For example, implantation can be guided using MRI, CT, ultrasound, or other modalities.

An image of the location is then generated in an MRI modality. In addition, another image of the location can be generated in another imaging modality, such as a CT X-ray imaging modality. Other imaging modalities may be employed, such as ultrasound, X-ray, fluoroscopy, electrical impedance tomography, magnetic source imaging (MSI), magnetic resonance spectroscopy (MRS), magnetic resonance mammography (MRM), magnetic resonance angiography (MRA), magnetoelectroencephalography (MEG), laser optical imaging, electric potential tomography (EPT), brain electrical activity mapping (BEAM), arterial contrast injection angiography, digital subtraction angiography, positron emission tomography (PET), and single photon emission computed tomography (SPECT).

If multiple imaging modalities are employed, positional information for the area of the body that was imaged can be determined as a function of the images thus generated. For example, the images can be registered so as to align the coordinate systems of the images. In this way, any point in the imaged area of the body is made to correspond to identical addresses in each image. This registration process involves the use of rigid body transformation techniques, which in three-dimensional images requires knowledge of at least three points in each image. The markers described above may serve as fiducial markers to mark these points in the images. Accordingly, the fiducial markers can be used to correlate the spaces in each image, both with respect to physical space and with respect to the other images. In addition, the fiducial markers provide a constant frame of reference that is visible in each imaging modality to facilitate registration.

As demonstrated by the foregoing discussion, various embodiments may provide certain advantages, particularly in the context of imaging heterogeneous breast tissue. For instance, the use of a mixture of an MR contrast agent and a CT contrast agent may promote visibility in multiple imaging modalities, thus facilitating registering images obtained by multimodal imaging procedures. A contrast agent selected to produce an increase in signal intensity in an MR imaging modality may produce good visualization characteristics without also producing an excessive artifact and without interfering with MR spectroscopy or diffusion imaging. By producing an increase in signal intensity in MR imaging, the implantable tissue markers disclosed herein may be easier to see than conventional markers.

Because the contrast agents are sealed within the tube or capsule, they are at least substantially permanent and are not absorbed by the patient's body. Thus, multimodal imaging using the markers disclosed herein also allows a clinician to monitor an anatomical site over a period of time using images from multiple modalities, if desired. If the anatomical site in question requires treatment, the markers can be used to determine the precise location of the anatomical site and thus guide therapy. For example, markers can be implanted at a lesion site prior to removing the lesion to guide the procedure. After the lesion is removed, the markers can be used to monitor the site overtime.

It will be understood by those who practice the embodiments described herein and those skilled in the art that various modifications and improvements may be made without departing from the spirit and scope of the disclosed embodiments. For example, the markers disclosed herein may incorporate therapeutic agents, such as radioactive agents, anti-inflammatory agents, anti-microbial agents, hemostatic agents, biocompatible adhesives, proteins, stem cells, or other material. Such agents may be applied to an external surface of the markers or disposed within the internal chambers. Accordingly, the scope of protection afforded is to be determined solely by the claims and by the breadth of interpretation allowed by law.

Figure 7:
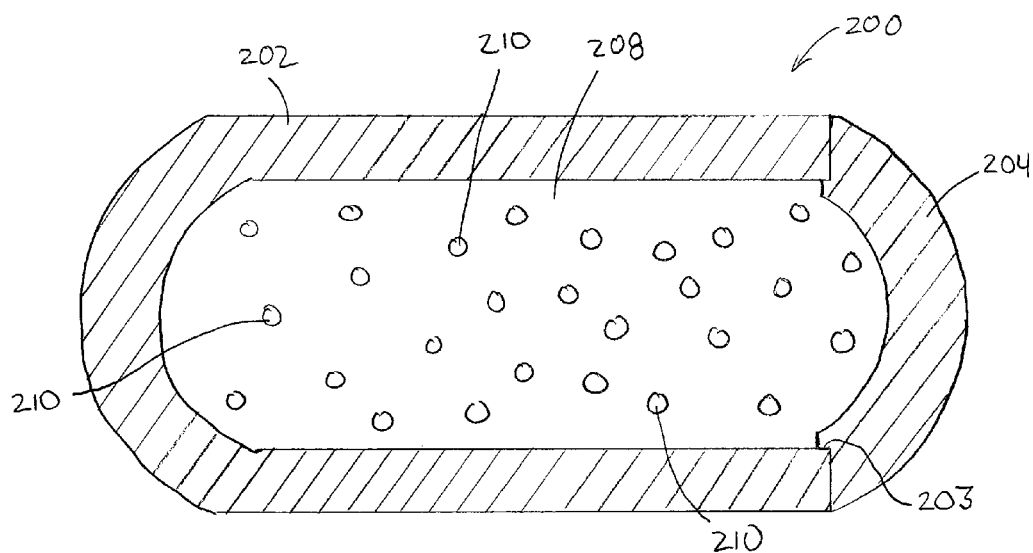
FIG. 7 is a sectional view of a tissue marker according to an embodiment.
Figure 8:
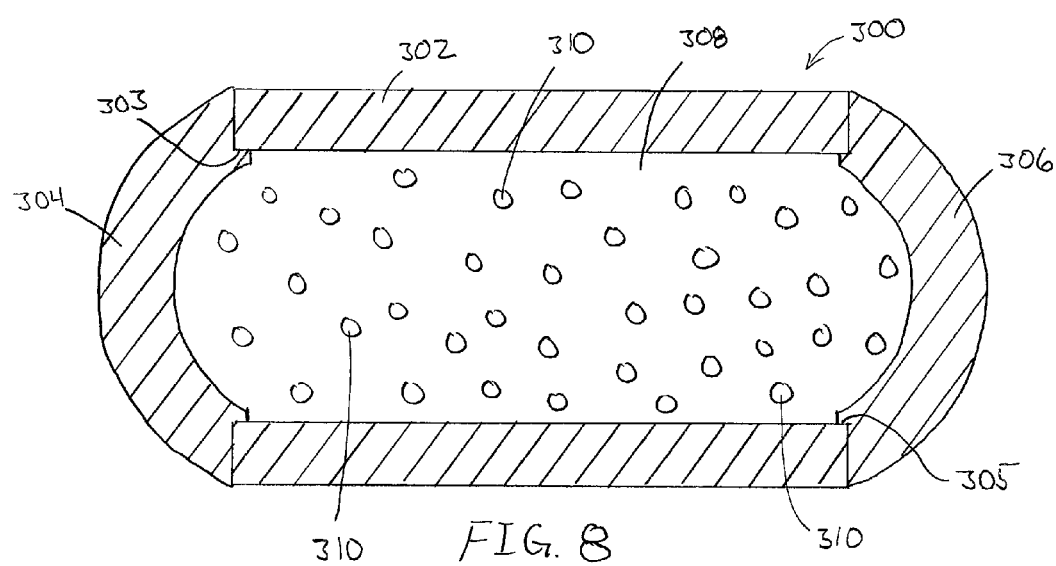
FIG. 8 is a sectional view of a tissue marker according to an embodiment.

Referring to FIGS. 7 and 8, additional examples of implantable radiographic markers 200, 300 are shown. The markers 200, 300, in various examples, can be formed from materials and in manners similar to those discussed herein.

Referring to FIG. 7, briefly, in some examples, the marker 200 includes a fully implantable, biocompatible container 202 formed from a nonbiodegradable solid material and defining an internal chamber 208. In this example, the container 202 includes an opening 203. In a further example, the container 202 is substantially vial-shaped. The marker 200, in an example, includes a lid portion 204 configured to be attached to the container 202 to close the opening 203. In an example, the lid portion 204 is configured to seal the opening 203. In an example, the marker 200 is sized for insertion via a biopsy cannula.

In some examples, one or more contrast agents 210 are introduced into the chamber 208. The opening 203, in an example, is sealed with the lid portion 204 to seal the contrast agent 210 within the chamber 208. In some examples, the opening 203 can be sealed in various ways, including press-fitting the lid portion 204 within the opening 203 of the container 202, using sealant or epoxy, or using other sealing techniques, such as, for instance ultrasonic welding of the lid portion 204 and the container 202. The visual representation of the contrast agents 210 in FIG. 7 is intended only to distinguish the contrast agents 210 from the chamber 208 in which they are disposed. According to various examples, the contrast agents 210 can be implemented as a gas, gel, or liquid, or as a combination of gases, gels, and/or liquids. Each of these materials can be selected independently to customize the appearance of the marker 200 in different imaging modalities and under different conditions, for instance, with or without contrast or in various tissue types. For instance, various contrast agents 210 or combinations of contrast agents 210, as described herein with respect to other examples, can be used for different imaging conditions, imaging modalities, tissue types, etc.

In an example, the marker 200 is formed by injection molding the container 202 and the lid portion 204. In another example, the marker 200 can be formed by micromachining. In a further example, the marker 200 can be encapsulated by a material, such as, for instance, silicone, PTFE, or another substance capable of performing as described herein. Such encapsulation, in various examples, can improve the seal of the marker 200; improve the bio-compatibility of the marker 200; can improve the surface properties of the marker 200, for instance, to facilitate deployment of the marker 200 through trocar or other device; or reduce bio-mobility of the marker 200 once it is implanted.

Referring to FIG. 8, briefly, in some examples, the marker 300 includes a fully implantable, biocompatible container 302 formed from a nonbiodegradable solid material and defining an internal chamber 308. In this example, the container 302 includes two openings 303, 305. In a further example, the container 302 is substantially tube-shaped. The marker 300, in an example, includes two lid portions 304, 306 configured to be attached to the container 302 to close the openings 303, 305. In an example, the lid portions 304, 306 are configured to seal the openings 303, 305. In an example, the marker 300 is sized for insertion via a biopsy cannula.

In some examples, one or more contrast agents 310 are introduced into the chamber 308. The openings 303, in an example, are sealed with the lid portions 304, 306 to seal the contrast agent 310 within the chamber 308. In some examples, the openings 303, 305 can be sealed in various ways, including press-fitting the lid portions 304, 306 within the openings 303, 305 of the container 302, using sealant or epoxy, or using other sealing techniques, such as, for instance ultrasonic welding of the lid portions 304, 306 and the container 302. The visual representation of the contrast agents 310 in FIG. 8 is intended only to distinguish the contrast agents 310 from the chamber 308 in which they are disposed. According to various examples, the contrast agents 310 can be implemented as a gas, gel, or liquid, or as a combination of gases, gels, and/or liquids. Each of these materials can be selected independently to customize the appearance of the marker 300 in different imaging modalities and under different conditions, for instance, with or without contrast or in various tissue types. For instance, various contrast agents 310 or combinations of contrast agents 310, as described herein with respect to other examples, can be used for different imaging conditions, imaging modalities, tissue types, etc.

In an example, the marker 300 is formed by injection molding the container 302 and the lid portions 304, 306. In another example, the marker 300 can be formed by micromachining. In a further example, the marker 300 can be encapsulated by a material, such as, for instance, silicone, PTFE, or another substance capable of performing as described herein. Such encapsulation, in various examples, can improve the seal of the marker 300; improve the bio-compatibility of the marker 300; can improve the surface properties of the marker 300, for instance, to facilitate deployment of the marker 300 through trocar or other device; or reduce bio-mobility of the marker 300 once it is implanted.

With reference to FIGS. 1-8, further examples include methods of manufacturing radiographic markers 100, 120, 130, 200, 300 capable of being permanently implanted in a living human or animal subject. In various examples, the fully implantable, biocompatible container 102, 122, 132, 202, 302 is formed from a nonbiodegradable solid material. In some examples, the container 102, 122, 132, 202, 302 is formed to define an internal chamber 108, 124, 134, 208, 308. In some examples, the contrast agent 110, 126, 136, 210, 310 is sealed within the internal chamber 108, 124, 134, 208, 308. In various examples, the contrast agent 110, 126, 136, 210, 310 is configured to produce a change in signal intensity in at least a magnetic resonance (MR) imaging modality with the marker 100, 120, 130, 200, 300 fully implanted in the subject. In an example, the solid material of the container 102, 122, 132, 202, 302 includes a first magnetic susceptibility and the contrast agent 110, 126, 136, 210, 310 includes a second magnetic susceptibility. In a further example, the solid material and the contrast agent 110, 126, 136, 210, 310 are configured such that the first and second magnetic susceptibilities are matched so that the first magnetic susceptibility is substantially equivalent to the second magnetic susceptibility. In some examples, the permanently implantable radiographic marker 100, 120, 130, 200, 300 is sized and shaped to fit within a lumen of a cannula configured to deliver the marker 100, 120, 130, 200, 300 to a fully implanted location within the subject.

In several examples, the method includes at least partially filling the internal chamber 108, 124, 134, 208, 308 with the contrast agent 110, 126, 136, 210, 310. Such filling can be accomplished in various manners including, but not limited to those described herein. In an example, the container 102, 122, 132, 202, 302 can be immersed within the contrast agent 110, 126, 136, 210, 310 to inhibit gas from being sealed within the internal chamber 108, 124, 134, 208, 308. In a further example, the container 102, 122, 132, 202, 302 is sealed while the container 102, 122, 132, 202, 302 is immersed in the contrast agent 110, 126, 136, 210, 310 to further inhibit unwanted materials from being sealed within the internal chamber 108, 124, 134, 208, 308 of the container 102, 122, 132, 202, 302. In an example, the container 102, 122, 132, 202, 302 can be immersed within a vat, receptacle, tank, etc. of the contrast agent 110, 126, 136, 210, 310 in order to lessen the amount of air or another gas from being present within the internal chamber 108, 124, 134, 208, 308 prior to sealing of the container 102, 122, 132, 202, 302. In some examples, the internal chamber 108, 124, 134, 208, 308 is at least partially filled with the contrast agent 110, 126, 136, 210, 310 with the container 102, 122, 132, 202, 302 within a chamber filled with a gas other than ambient air to inhibit ambient air from being sealed within the internal chamber 108, 124, 134, 208, 308. In an example, the chamber within which the container 102, 122, 132, 202, 302 is filled includes air or another gas at a pressure other than ambient pressure. For instance, the container 102, 122, 132, 202, 302 can be filled in a vacuum, in a high pressure environment, or in a pressure therebetween. In some examples, the internal chamber 108, 124, 134, 208, 308 can be filled with the contrast agent 110, 126, 136, 210, 310 with the container 102, 122, 132, 202, 302 within a chamber substantially filled with a gas other than air. In a further example, the internal chamber 108, 124, 134, 208, 308 can be filled with the container 102, 122, 132, 202, 302 within the chamber substantially filled with nitrogen. For instance, in certain examples, oxygen (present in air) can be undesirable due to magnetic properties that could make susceptibility matching of the marker 100, 120, 130, 200, 300 more difficult than if oxygen were not present. In this example, filling of the container 102, 122, 132, 202, 302 with the contrast agent 110, 126, 136, 210, 310 within a nitrogen-filled chamber would cause residual gas bubbles within the container 102, 122, 132, 202, 302 to be nitrogen rather than oxygen, which can be more desirable in certain examples due to the different magnetic properties of nitrogen than those of oxygen. However, in other examples, the presence of oxygen within the container 102, 122, 132, 202, 302 can be desirable. In these examples, by adjusting the mixture of air or other gas or gases, the magnetic susceptibility and, therefore, the MRI visibility, of the marker 100, 120, 130, 200, 300 can be adjusted.

In some examples, the container 102, 122, 132, 202, 302 is vibrated during filling to aid in removal of gas bubbles from within the internal chamber 108, 124, 134, 208, 308 prior to sealing of the container 102, 122, 132, 202, 302. Such vibration can cause gas bubbles within the contrast agent 110, 126, 136, 210, 310 to rise out of the contrast agent 110, 126, 136, 210, 310 and toward an opening in the container 102, 122, 132, 202, 302, so that the gas bubbles can exit the container 102, 122, 132, 202, 302 prior to sealing of the container 102, 122, 132, 202, 302. In an example, the container 102, 122, 132, 202, 302 is ultrasonically vibrated in order to aid in removal of gas bubbles from within the internal chamber 108, 124, 134, 208, 308 prior to sealing of the container 102, 122, 132, 202, 302.

The various examples of filling of the container 102, 122, 132, 202, 302 described herein can be used to introduce or decrease amounts of various contrast agent materials within the internal chamber 108, 124, 134, 208, 308 of the container 102, 122, 132, 202, 302, based upon the desired mix of the contrast agent, the desired purity of the contrast agent, the desired response of the contrast agent in various imaging modalities, or the like. In this way, the filling environment and/or the contrast agent 110, 126, 136, 210, 310 within the container 102, 122, 132, 202, 302 can be controlled to tune the response of the marker 100, 120, 130, 200, 300 in one or more of various imaging modalities. The described examples of filling of the container 102, 122, 132, 202, 302 are meant to be illustrative and are not intended to be limiting. As such, additional techniques and methods of filling the container 102, 122, 132, 202, 302 are contemplated herein.

In some examples, the method includes mixing a first contrast agent configured to produce the change in signal intensity in the MR imaging modality and a second contrast agent configured to produce a signal in another imaging modality. In an example, the other imaging modality includes a computed tomographic (CT) X-ray imaging modality. In other examples, the other imaging modality includes one of an ultrasound imaging modality, an X-ray imaging modality, a fluoroscopy imaging modality, an electrical impedance tomographic imaging modality, a magnetic source imaging (MSI) modality, an magnetic resonance spectroscopic (MRS) modality, a magnetic resonance mammographic (MRM) modality, a magnetic resonance angiographic (MRA) modality, a magnetoelectroencephalographic (MEG) modality, a laser optical imaging modality, an electric potential tomographic (EPT) modality, a brain electrical activity mapping (BEAM) modality, an arterial contrast injection angiographic modality, a digital subtraction angiographic modality, a positron emission tomographic (PET) modality, and a single photon emission computed tomographic (SPECT) modality. In an example, the contrast agent 110, 126, 136, 210, 310 includes the mixture of the first and second contrast agents. In this example, the mixture of the first and second contrast agents is sealed within the internal chamber 108, 124, 134, 208, 308. In other examples, any number of contrast agents can be mixed together, depending upon the application for which the marker 100, 120, 130, 200, 300 is to be used. In an example, the first contrast agent includes a paramagnetic material. In another example, the first contrast agent includes gadolinium. In a further example, the second contrast agent includes iodine. In various examples, the contrast agent 110, 126, 136, 210, 310 includes at least one of a gas material, a liquid material, or a gel material.

In another example, the method includes sealing a therapeutic agent within the internal chamber 108, 124, 134, 208, 308.

In an example, the method includes forming the container 102, 122, 132, 202, 302 from a solid material configured to produce a signal in an imaging modality other than MR, including, but not limited to other imaging modalities described herein.

In various examples, the method includes forming the container 102, 122, 132, 202, 302 in various ways. In an example, the container 102, 122, 132, 202, 302 is molded. In a further example, the container 102, 122, 132, 202, 302 is injection molded. In a still further example, the container 102, 122, 132, 202, 302 is micromachined. The above examples are intended to be illustrative, not limiting, as it is contemplated that the container 102, 122, 132, 202, 302 can be formed in manners or using techniques other than those described herein, depending upon factors including the materials, size, shape, etc. of the marker 100, 120, 130, 200, 300.

In such examples, the container 102, 122, 132, 202, 302 can be formed from various materials. In some examples, the container 102, 122, 132, 202, 302 is formed from a polymeric material. In a further example, the container 102, 122, 132, 202, 302 is formed from a polyether material. In still further examples, the container 102, 122, 132, 202, 302 is formed from a material including at least one of polytetrafluoroethylene (PTFE), polyether ether ketone (PEEK), polysulfone, polyurethane, and polyethylene. In another example, the container 102, 122, 132, 202, 302 is formed from a silicone-based material. The above examples are intended to be illustrative, not limiting, as it is contemplated that the container 102, 122, 132, 202, 302 can be formed from materials other than those described herein, depending upon the use and desired properties of the marker 100, 120, 130, 200, 300.

In some examples, the method includes forming the tube 102 defining the first and second end portions 104, 106. In an example, the contrast agent 110 is sealed within the internal chamber 108 includes at least substantially sealing the first and second end portions 104, 106 using the biocompatible adhesive 112. In further examples, the tube 102 is formed from a solid material including at least one of a glass material, a ceramic material, a polymer material, silicone, or carbon fiber.

In some examples, the method includes forming a vial-shaped portion 202 of the container 202. In this example, the vial-shaped portion 202 includes the opening 203. In an example, the lid portion 204 of the container 202 is also formed. In this example, the lid portion 204 of the container 202 is configured to be attached at the opening 203 of the vial-shaped portion 202 of the container 202.

In some examples, the method includes forming a first portion 302 including at least two openings 303, 305. In this example, second and third portions 304, 306 are formed and are configured to be attached to the first portion 302 at the at least two openings 303, 305. In an example, the first portion 302 is substantially tube-shaped. In an example, the second and third portions 304, 306 are attached at the respective openings 303, 305 of the first portion 302 to seal the contrast agent 310 within the internal chamber 308. In other examples, the first portion includes other shapes, such as, but not limited to, substantially spherical, substantially ellipsoidal, substantially prismatic, etc. In other examples, the first portion can include more or less than two openings.

In some examples, the method includes coating the marker 100, 120, 130, 200, 300 to encapsulate the marker 100, 120, 130, 200, 300. In an example, the marker 100, 120, 130, 200, 300 is fully encapsulated with a material to improve the seal of the marker 100, 120, 130, 200, 300; improve the biocompatibility of the marker 100, 120, 130, 200, 300; can improve the surface properties of the marker 100, 120, 130, 200, 300, for instance, to facilitate deployment of the marker 100, 120, 130, 200, 300 through trocar or other device; or reduce bio-mobility of the marker 100, 120, 130, 200, 300 once it is implanted. In an example, such encapsulation hermetically seals the marker 100, 120, 130, 200, 300. Various materials are contemplated for encapsulating the marker 100, 120, 130, 200, 300. For instance, in some examples, the marker 100, 120, 130, 200, 300 can be coated with a material including at least one of silicone or PTFE.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A fully implantable, biocompatible, fiducial marker capable of being implanted in a living human or animal subject, the fiducial marker comprising:
   a container wall formed from a nonbiodegradable solid material defining an internal chamber; and
   a sensing medium sealed within the internal chamber, the sensing medium including at least one of a liquid, a gas portion, and a solid portion, wherein the sensing medium is configured to produce a detectable signal in a magnetic resonance (MR) imaging modality with the fiducial marker fully implanted in the subject, wherein the nonbiodegradable solid material of the container includes a first magnetic susceptibility and the sensing medium includes a second magnetic susceptibility, wherein the nonbiodegradable solid material and the sensing medium are configured such that the first and second magnetic susceptibilities are matched so that the first magnetic susceptibility is substantially equivalent to the second magnetic susceptibility.

2. The fiducial marker of claim 1, wherein the gas is other than ambient air to inhibit ambient air from being sealed within the internal chamber.

3. The fiducial marker of claim 2, wherein the gas includes nitrogen.

4. The fiducial marker of claim 1, wherein the gas includes a mixture of ambient air and one or more other gases.

5. The fiducial marker of claim 1, wherein the gas includes ambient air.

6. The fiducial marker of claim 1, wherein the gas includes nitrogen and one or more other gases.

7. The fiducial marker of claim 1, wherein the liquid portion of the sensing medium is configured to produce a detectable signal in the MR imaging modality and the gas portion is configured to produce a signal in another imaging modality.

8. The fiducial marker of claim 7, wherein the other imaging modality includes an ultrasound based imaging modality.

9. The fiducial marker of claim 1, wherein the gas is dispersed within the liquid.

10. The fiducial marker of claim 1, wherein the fully implantable biocompatible container is configured to produce a detectable signal in at least one imaging modality, including at least one of MR, ultrasound, and x-ray.

11. The fiducial marker of claim 1, wherein a solid portion of the sensing medium is configured to produce a detectable signal under one or more imaging modalities.

12. The fiducial marker of claim 1, wherein the fully implantable, biocompatible container includes a tube defining first and second end portions, and wherein the first end portion and the second end portion includes a biocompatible seal to seal the sensing medium within the internal chamber.

13. The fiducial marker of claim 1, wherein the fully implantable, biocompatible container includes a solid material including at least one of a glass material, a ceramic material, a polymer material, silicone, or carbon fiber or other composite material.

14. The fiducial marker of claim 1, wherein the fully implantable, biocompatible container has a vial-shaped portion, the vial-shaped portion including an opening.

15. The fiducial marker of claim 14, wherein the fully implantable, biocompatible container includes a lid portion.

16. The fiducial marker of claim 15, wherein the lid portion is attached to the opening of the vial-shaped portion.

17. The fiducial marker of claim 16, wherein the second portion is attached to a first opening of the at least two openings and the third portion is attached to a second opening of the at least two opening.

18. The fiducial marker of claim 17, wherein the coating hermetically seals the fully implantable, biocompatible container.

19. The fiducial marker of claim 1, wherein the fully implantable, biocompatible container includes:
a first portion including at least two openings; and
a second and third portion configured to be attached to the first portion at the at least two openings.

20. The fiducial marker of claim 1, comprising a coating on an external surface of the fully implantable, biocompatible container, the coating encapsulating the fully implantable, biocompatible container.

21. The fiducial marker of claim 1, wherein the radiographic marker is sized and shaped to fit within a lumen of a cannula configured to deliver the marker to a fully implanted location within the subject.

22. A method of manufacturing a fiducial marker capable of being implanted in a living human or animal subject, the method comprising:
forming a fully implantable, biocompatible container from a nonbiodegradable solid material, the fully implantable, biocompatible container defining an internal chamber;
at least partially filling the internal chamber with a sensing medium including at least one of a liquid, a gas portion and a solid portion, wherein the sensing medium is configured to produce a detectable signal in a magnetic resonance (MR) imaging modality with the fiducial marker fully implanted in the subject, wherein the nonbiodegradable solid material of the fully implantable, biocompatible container includes a first magnetic susceptibility and the contrast agent includes a second magnetic susceptibility, wherein the nonbiodegradable solid material and the contrast agent are configured such that the first and second magnetic susceptibilities are matched so that the first magnetic susceptibility is substantially equivalent to the second magnetic susceptibility; and
sealing the sensing medium within the internal chamber.

23. The method of claim 22, wherein at least partially filling the internal chamber includes at least partially filling the internal chamber in a pressurized gas controlled environment.

24. The method of claim 22, wherein the gas is other than ambient air to inhibit ambient air from being sealed within the internal chamber.

25. The method of claim 22, wherein the gas is nitrogen.

26. The method of claim 22, wherein the gas is a mixture of ambient air and one or more other gases.

27. The method of claim 22, wherein the gas is ambient air.

28. The method of claim 22, wherein the gas is nitrogen and one or more other gases.

29. The method of claim 22, comprising mixing the liquid configured to produce a detectable signal in the MR imaging modality and the gas configured to produce a detectable signal in another imaging modality, wherein sealing the sensing medium within the internal chamber includes sealing the mixture comprising at least one of the liquid, solid or the gas within the internal chamber.

30. The method of claim 22, wherein the fully implantable, biocompatible container includes a first portion and a second portion, the first portion including at least one opening configured to access the internal chamber, and wherein sealing the sensing medium within the internal chamber includes attaching the second portion at the opening of the first portion.

31. The method of claim 22, wherein the fully implantable, biocompatible container includes: a first portion including at least two openings; and a second portion and a third portion configured to be attached to the first portion at the at least two openings, wherein sealing the sensing medium within the internal chamber includes attaching the second and third portions at respective openings of the first portion.

32. The method of claim 22, wherein the fully implantable, biocompatible container includes a first end portion including at least one opening, and wherein sealing the sensing medium within the internal chamber includes sealing the first end portion using a biocompatible adhesive or other sealing method.

33. The method of claim 22, comprising coating the fully implantable, biocompatible container to encapsulate the fully implantable, biocompatible container.

34. The method of claim 22, comprising at least partially filling the internal chamber with the sensing medium within a chamber at a pressure other than ambient pressure.

35. The method of claim 22, comprising including a therapeutic agent within the internal chamber of the fully implantable, biocompatible container.

36. The method of claim 22, comprising applying a therapeutic agent to an external surface of the fully implantable, biocompatible container.

37. A method of medical imaging or treatment using a fiducial marker capable of being implanted in a living human or animal subject, the method comprising:
performing medical imaging or treatment on a subject using a fully implantable, biocompatible container formed from a nonbiodegradable solid material, the fully implantable, biocompatible container defining an internal chamber; and
producing a detectable signal in a magnetic resonance (MR) imaging modality, with the internal chamber at least partially filled with a sensing medium sealed within the internal chamber, the sensing medium including at least one of a liquid, a gas portion and a solid portion, wherein the sensing medium is configured to produce a detectable signal in a magnetic resonance (MR) imaging modality with the fiducial marker fully implanted in the subject, wherein the nonbiodegradable solid material of the fully implantable, biocompatible container includes a first magnetic susceptibility and the contrast agent includes a second magnetic susceptibility, wherein the nonbiodegradable solid material and the contrast agent are configured such that the first and second magnetic susceptibilities are matched so that the first magnetic susceptibility is substantially equivalent to the second magnetic susceptibility.

* * * * *